United States Patent
Gerkens et al.

(10) Patent No.: US 10,392,603 B2
(45) Date of Patent: Aug. 27, 2019

(54) METHOD OF VIRAL PURIFICATION

(71) Applicants: GlaxoSmithKline Biologicals S.A., Rixensart (BE); The Chemo-Sero-Therapeutic Research Institute, Kumamoto (JP)

(72) Inventors: Pascal Charles Louis Gerkens, Rixensart (BE); Michele Therese Rita Lecocq, Rixensart (BE); Tatsuya Kasugaya, Kumamoto (JP); Kenjiro Kawatsu, Kumamoto (JP); Yoshinobu Miyatsu, Kumamoto (JP); Tetsuro Tanabe, Kumamoto (JP)

(73) Assignee: The Chemo-Sero-Therapeutic Research Institute, Kumamoto (JP)

( * ) Notice: Subject to any disclaimer, the term of this patent is extended or adjusted under 35 U.S.C. 154(b) by 97 days.

(21) Appl. No.: 14/914,341

(22) PCT Filed: Aug. 28, 2014

(86) PCT No.: PCT/EP2014/068248
§ 371 (c)(1),
(2) Date: Feb. 25, 2016

(87) PCT Pub. No.: WO2015/028546
PCT Pub. Date: Mar. 5, 2015

(65) Prior Publication Data
US 2016/0208220 A1  Jul. 21, 2016

Related U.S. Application Data

(60) Provisional application No. 61/872,024, filed on Aug. 30, 2013.

(51) Int. Cl.
*C12N 7/00* (2006.01)
*A61K 39/145* (2006.01)
*A61K 39/12* (2006.01)
*A61K 39/00* (2006.01)

(52) U.S. Cl.
CPC .............. *C12N 7/00* (2013.01); *A61K 39/12* (2013.01); *A61K 39/145* (2013.01); *A61K 2039/525* (2013.01); *C12N 2760/16034* (2013.01); *C12N 2760/16051* (2013.01); *C12N 2760/16151* (2013.01); *C12N 2760/16251* (2013.01)

(58) Field of Classification Search
None
See application file for complete search history.

(56) References Cited

FOREIGN PATENT DOCUMENTS

| EP | 1985305 | * | 10/2008 |
|---|---|---|---|
| EP | 1985305 A1 | | 10/2008 |
| WO | 02/28422 A2 | | 4/2002 |
| WO | 2011/012725 A1 | | 2/2011 |
| WO | WO 2011/012725 | * | 2/2011 |

OTHER PUBLICATIONS

Stoker, Masters Thesis Utah State University 2011.*
Weber, et al., "Supplement Development and Qualification of a Scalable, Disposable Bioreactor for GMP-Compliant Cell Culture Suppliers Put Quality by Design Concepts into Practice" BioProcess International; Apr. 1, 2013; pp. 6-17; vol. 11, No. 4(s).
Stoker, "Comparative studies on scale-up methods of single-use bioreactors" Retrieved from the Internet: URL: http://search.proquest. com/docview/862348141; Jan. 1, 2011; pp. 1-97; p. 2, line 8-line 12, p. 91, last paragraph—p. 92, paragraph 1.

* cited by examiner

*Primary Examiner* — Shanon A. Foley
*Assistant Examiner* — Myron G Hill
(74) *Attorney, Agent, or Firm* — Eric J. Kron

(57) ABSTRACT

A method of producing a virus in cell culture comprising at least the steps of a) providing a population of cells cultured in a cell culture medium, b) infecting the population of cells by i. inoculating the population with the virus, and ii. incubating the inoculated population so as to allow the virus to replicate and propagate, c) collecting the produced virus, thereby providing a viral harvest, and d) purifying the virus, wherein a power density of at least 15 $W/m^3$, at least 30 $W/m^3$, at least 60 $W/m^3$, at least 100 $W/m^3$, at least 120 $W/m^3$ is applied to the cell culture at least during step b).

28 Claims, No Drawings

METHOD OF VIRAL PURIFICATION

STATEMENT REGARDING FEDERALLY SPONSORED RESEARCH

This invention was made with United States government support under Contract # HHSO100200600011C awarded by the Department of Health and Human Services; the United States government has certain rights in the invention.

This application is filed pursuant to 35 U.S.C. § 371 as a U.S. National Phase Application of International Patent Application Serial No. PCT/EP2014/068248 filed 28 Aug. 2014, which claims the benefit of U.S. Provisional 61/872,024 filed 30 Aug. 2013.

TECHNICAL FIELD

The present invention relates to a method for producing viruses, or viral antigens, produced by cell culture, to the viruses or viral antigens obtainable by this method and to vaccines which contain such viruses or viral antigens. In particular, the invention provides a method for improving the virus yield.

BACKGROUND

The development of cell culture-based technologies as an alternative to the traditional egg-based production systems for the manufacture of viral vaccines likely appears as the most rapid and most promising solution to overcome drawbacks and constraints associated with egg-based traditional systems. Commercial productions of viral vaccines typically require large quantities of virus as an antigen source. However, the egg-based process is vulnerable due to the varying biological quality of eggs and it lacks flexibility because of the logistic problems due to non-availability of large quantities of suitable eggs.

Cell culture systems appear as a suitable alternate mode of vaccine preparation, simpler, flexible, and consistent, allowing to improve possibilities of up-scaling vaccine production capacities and thus to reach large quantities of virus, if needed. For example, in response to a natural pandemic threat or a to a terrorist attack.

However, efficient vaccine production requires the growth of large scale quantities of virus produced in high yields from a host system. The cultivation conditions under which a virus is grown is of great significance with respect to achieving an acceptable high yield of the virus. Thus, in order to maximise the yield of the desired virus, both the system and the cultivation conditions must be adapted specifically to provide an environment which is advantageous for the production of the desired virus which is suitable for large scale production. One way is to improve the cell specific productivity, for example, by improving the culture medium, or increasing the cell density. Due to the fact that, after production, the cell culture-produced virus must be recovered from the cell culture and purified, another way to improve virus yield is to limit the virus material loss occurring along the different purification steps. Therefore, a need remains for providing alternative and improved methods to produce viruses with an increased virus yield. The method according to the present invention provides a better virus yield over the methods known in the art.

SUMMARY OF THE INVENTION

In a first aspect of the present invention, there is provided a method of producing a virus in cell culture comprising at least the steps of:

a) providing a population of cells in a cell culture medium,
b) infecting the population of cells by:
 i. inoculating the population with the virus, and
 ii. incubating the inoculated population so as to allow the virus to replicate and propagate,
c) collecting the produced virus, thereby providing a viral harvest, and
d) purifying the virus,
wherein a volumetric power input of at least 15 W/m$^3$, at least 30 W/m$^3$, at least 60 W/m$^3$, at least 100 W/m$^3$, or at least 120 W/m$^3$ is applied to the cell culture at least during step b).

In a second aspect of the present invention, there is provided a method for the preparation of a vaccine comprising at least the step of admixing the virus obtained according to the method of the present invention with a pharmaceutically acceptable carrier.

DETAILED DESCRIPTION

The present invention relates to an improved method of producing viruses in cell culture, which is particularly useful for large scale production. In particular, the method according to the invention helps increase the virus yield by limiting virus loss during the purification process. The inventors surprisingly observed that some changes happening in the upstream part of the virus production process, such as increasing the volumetric power input applied to the cultured cells used to produce a virus, resulted in a significant improvement in the downstream part of said process, such as an increase of the virus yield obtained after some purification steps. In particular, the inventors observed that, while increasing the power input during the upstream cell culture phase had no impact on the cell specific productivity, a positive impact on a subsequent step of clarification by microfiltration was obtained in that the virus yield obtained after said step was significantly increased, as compared with the yield obtained when a lower power input was implemented during the cell culture phase. Moreover, not only was the virus recovery after the microfiltration step increased, but also the recovery percentages obtained were more consistent and less variable from one experiment to another. Also, the inventors observed a similar beneficial effect of increasing the volumetric power input during the upstream cell culture phase on a subsequent sucrose gradient ultracentrifugation step implemented during the downstream virus purification phase. In particular, the inventors observed that increasing the volumetric power input applied to the cultured cells allowed to significantly increase, by about a factor of 2, the load capacity of the rotor used for the sucrose gradient ultracentrifugation step. As a consequence, the improved virus yield obtained after some purification steps led to a better global yield of the virus at the end of virus production process. Unexpectedly, the inventors observed that a higher volumetric power input did not cause harm or damage to the cells.

The method according to the present invention provides the advantage to be easy to implement, as no extra-step or no further equipment other than the standard ones typically used for producing a virus in cell culture are required.

"Load capacity" is the amount of viral harvest litres collected during step c) of the method of the invention which is loaded per litre of rotor of the centrifuge used for the sucrose gradient ultracentrifugation step, or the "equivalent" amount of viral harvest litres when said viral harvest has been treated before being subject to the sucrose gradient ultracentrifugation step, due to prior purification steps. For example, as described below, after being collected, the viral harvest may be subject to ultrafiltration/diafiltration before being subject to a sucrose gradient ultracentrifugation step, which ultrafiltration/diafiltration typically results in the concentration of the viral harvest, i.e. the amount of viral harvest litres is reduced after such a step.

"Volumetric power input" is the amount of power per unit volume, or the mean specific energy dissipation rate. In cell culture, it corresponds to the amount of power transferred to a volume of cell culture through the agitator shaft and impellers. It is expressed as $W/m^3$. The empiric formula used in the art to calculate power input values is as follows: $P/V=(Np \times n^3 \times di^5)/V$, where Np is the turbulent power number for the impeller, n is the stirring rate measured as impeller revolutions per second, di is the impeller diameter measured in meter and V is the culture volume in cubic meters.

The method according to the present invention is applicable to any type of cells, whether adherent cells grown on micro-carriers or suspension cells. Accordingly, in the sense of the present invention, the terms "cell suspension" shall encompass both adherent cells grown on micro-carriers and cells able to grow in suspension, i.e. that do not require any adherent support, such as micro-carriers, to grow.

Typically, volumetric power input is applied by a mechanical movement of the cell suspension. Said mechanical movement may be achieved through different means. For example, the mechanical movement of the cell suspension can be achieved by means of an agitation device, such as impellers.

Agitation can be imparted as an axial flow, a radial flow, or a combination of the two, depending on the impeller type which is used. Typically, impellers can be divided into the following groups based on their geometry, and in particular, the geometry of their blades: (i) the flat-bladed turbines, also commonly referred to as Rushton impellers or Rushton-type impellers; (ii) the pitched-blade impellers; and (iii) the marine-blade impellers.

Flat-bladed turbines, or Rushton impellers, are made of flat blades which are set vertically along the agitation shaft, producing thus a unidirectional radial flow. Those types of impellers are commonly used in fermentations of cell lines that are not considered shear-sensitive, such as yeasts, bacteria, and some fungi. However, as disclosed therein, the inventors observed that Rushton impellers can also be suitably used with animal cells according to the method of the present invention.

Pitched-blade impellers are made of flat blades which are set at an angle in relation to the agitation shaft, producing thus simultaneous axial and radial flow. Such pitched-blade impellers are often used with shear-sensitive cell lines growing in suspension or with the aid of micro-carriers. These impellers are often used in batch or fed-batch cultures, but they can also be used for continuous and perfusion processes.

The leading face of the blades on a marine-blade impeller can be flat, or concave, whereas their back sides are convex, producing thus a unidirectional axial flow.

Different factors are to be taken into account to select the appropriate types of impellers such as, for example, the type of cells, the type of culture systems (batch, fed-batch or perfusion culture system), the type of culture vessels, as well as the level of volumetric power input which is desired. It is within the skilled person ambits to determine and select the appropriate impeller to use depending on the above specific conditions. In one embodiment, the volumetric power input, in particular volumetric power input ranging from 30 to 120 $W/m^3$, applied in the method according to the invention is achieved with a pitched-blade impeller. In another embodiment, the volumetric power input, in particular volumetric power input higher than 120 $W/m^3$, applied in the method according to the invention is achieved with a Rushton impeller.

The volumetric power input applied on animal cell cultures is typically much lower than that in microbial cultures because of the assumed higher fragility of animal cells which are devoid of a protective cell wall, making them in particular more sensitive to shear stress and foam formation than microbial cultures. However, as observed by the present inventors, the application of a high volumetric power input, to a certain extent, to animal cell cultures used for producing a virus does not harm the cells, while it advantageously favours the virus yield during the purification of the produced virus.

The method according to the invention may be implemented at a wide range of volumetric power input values. By "maximal value" is intended the maximal volumetric power input that can be applied in the absence of an overall negative impact on viral yield. One factor known to have a possible negative impact on viral yield is cell integrity, such as for instance decreased cell viability. The skilled person knows how to monitor cell viability. A non-limiting example of suitable methods is cell staining (allowing to discriminate living cells from dead cells), such as trypan blue staining, or any other known suitable staining. Alternatively, cell viability may also be evaluated and measured by flow cytometry, such as for instance, FACS (Fluorescence-Activated Cell Sorting). Also, when defining the maximal value, the cell specific productivity of the virus may be taken into account. By "cell specific productivity", it is meant the ability of cells to produce virus, i.e. the amount of virus achieved at the collecting step c), before being subject to purification. The volumetric power input applied to the cultured cells shall preferably not negatively affect the cell specific productivity of the virus.

By "minimal value" of volumetric power input is intended the minimal value providing an improvement of virus yield during the virus purification phase as compared to the virus yield obtained during the virus purification phase while no, or a low, volumetric power input is applied to the cultured cells. Any method known in the art to measure virus yield or virus titer can suitably be used to help determine optimal values of volumetric power input to be applied in the method of the invention. For example, the CPE (CytoPathic Effect) may be measured by monitoring the morphological changes occurring in host cells after virus inoculation, including cell rounding, disorientation, swelling or shrinking, death, detachment from the surface. Also, the detection of a specific viral antigen may be monitored by standard techniques of protein detection, such as a Western-blot analysis, at any time post-inoculation of the cells with the virus of interest to be produced. In the particular case of influenza virus, the content of HA may be monitored any time post-inoculation of the cells with the virus, by the SRD assay (Wood, J M, et al. (1977). J. Biol. Standard. 5, 237-247), which is a technique familiar to a person skilled in the art. Additionally, the SRD assay may also be used at any time during the purification phase in order to evaluate virus yield before and after any given purification step. In accordance with the method of the present invention, the volumetric power input applied to the animal cells used to produce viruses typically ranges from 15 to 900 $W/m^3$, suitably from 30 to 500 $W/m^3$, more suitably from 60 to 250 $W/m^3$, more suitably from 120 to 200 W/m³. In one embodiment, the volumetric power input value used in the method according to the invention is at least 15 W/m³, at least 30 W/m³, at least 60 W/m³, at least 100 W/m³, or at least 120 W/m³. In a specific embodiment, the volumetric power input value used in the method according to the invention is 30 W/m³. Alternatively, in another specific embodiment, the volumetric power input value used in the method according to the invention is 120 W/m³.

The method according to the invention is applicable to any type of cultivation vessels, of any size, such as for example, flasks, roller bottles, or bioreactors, so long as said vessels are either suitable for accommodating agitation devices, such as for example impellers, or are compatible with the use of a separate agitation device. It is not necessary that the vessel comprises an agitation device. The agitation device may be separate from the vessel itself. For example, in the case of disposable bioreactors, typically consisting of plastic bags, such as Wave™ bioreactors, agitation of said disposable bioreactors may be achieved by placing the bioreactors on an agitation table, whether an orbital shaker or an axial shaker. Bioreactors may be made of any type of materials, such as for example glass or stainless steel for non-disposable bioreactors, or plastic for disposable bioreactors. Also, bioreactors can be of any shape, such as for instance cylinder-shaped or cubic. Bioreactors are typically used for intermediate scale, such as from 1 to 10 L, and large production scale, such as from 20 to 1000 L, and beyond. The method according to the invention is applicable to any type of bioreactor of any size. In particular, the method of the invention is suitable for bioreactors of 10 L, 200 L, 500 L, 1000 L or 10000 L. One particularly suitable type of bioreactors for use in the method of the invention are stirred-tank bioreactors, whether operated in batch or in continuous. Disposable bioreactors represent an alternatively suitable type of bioreactors for use in the method of the invention. In one embodiment, the cells used in the method according to the present invention are cultured in a 200 L disposable bioreactor.

In accordance with the invention, cells may be grown in various ways, such as for example, using batch, fed-batch, or continuous systems, such as perfusion systems. Perfusion is particularly advantageous when high cell density is desired. High cell density may be particularly advantageous in order to maximise the amount of virus which can be produced from a given cell type. The method of producing a virus in cell culture wherein a high volumetric power input is applied to the cell culture in accordance with the present invention is applicable to any of the above systems, whether cells are grown using batch, fed-batch, or continuous systems. In one embodiment of the invention, the cells used according to the method of the present invention are grown in a batch mode.

The method of the invention is amenable to a wide range of viruses, any virus which is capable of infecting cells and using them for its replication, including, but not limited to, adenoviruses, hepadnaviruses, herpes viruses, orthomyxoviruses, papovaviruses, paramyxoviruses, picornaviruses, poxviruses, reoviruses and retroviruses. In particular, the method of invention is suitable for enveloped viruses, such as myxoviruses. In one embodiment, the viruses produced by the method of the invention belong to the family of orthomyxoviruses, in particular, influenza virus.

Viruses or viral antigens may be derived from an Orthomyxovirus, such as influenza virus. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase (PB1, PB2 and PA). Particularly suitable antigens include HA and NA, the two surface glycoproteins which determine the antigenic specificity of the Influenza subtypes.

The influenza virus can be selected from the group of human influenza virus, avian influenza virus, equine influenza virus, swine influenza virus, feline influenza virus. Influenza virus is more particularly selected in strains A, B and C, preferably from strains A and B.

Influenza antigens may be derived from interpandemic (annual or seasonal) influenza strains. Alternatively, influenza antigens may be derived from strains with the potential to cause a pandemic outbreak (i.e., influenza strains with new hemagglutinin compared to hemagglutinin in currently circulating strains, or influenza strains which are pathogenic in avian subjects and have the potential to be transmitted horizontally in the human population, or influenza strains which are pathogenic to humans). Depending on the particular season and on the nature of the antigen included in the vaccine, the influenza antigens may be derived from one or more of the following hemagglutinin subtypes: H1, H2, H3, H4, H5, H6, H7, H8, H9, H10, H11, H12, H13, H14, H15 or H16. Preferably, the influenza virus or antigens thereof are from H1, H2, H3, H5, H7 or H9 subtypes. In one embodiment, the influenza viruses are from H2, H5, H6, H7 or H9 subtypes. In an alternative embodiment, the influenza viruses are from H1, H3 or B subtypes.

The cells which are used in the method according to the invention can in principle be any desired type of animal cells which can be cultured in cell culture and which can support virus replication. They can be either primary cells or continuous cell lines. Genetically stable cell lines are preferred. Mammalian cells are particularly suitable, for example, human, hamster, cattle, monkey or dog cells. Alternatively, insect cells are also suitable, such as, for instance, SF9 cells or Hi-5 cells A number of mammalian cell lines are known in the art and include PER.C6, HEK cells, human embryonic kidney cells (293 cells), HeLa cells, CHO cells, Vero cells and MDCK cells.

Suitable monkey cells are, for example, African green monkey cells, such as kidney cells as in the Vero cell line. Suitable dog cells are, for example, kidney cells as in the MDCK cell line.

Suitable mammalian cell lines for growing influenza virus include MDCK cells, Vero cells, or PER.C6 cells. These cell lines are all widely available, for instance, from the American Type Cell Culture (ATCC) collection.

According to a specific embodiment, the method of the invention uses MDCK cells. The original MDCK cell line is available from the ATCC as CCL-34, but derivatives of this cell line may also be used, such as the MDCK cells adapted to growth in suspension (WO 1997/37000).

Alternatively, cell lines for use in the invention may be derived from avian sources, such as chicken, duck, goose, quail or pheasant. Avian cell lines may be derived from a variety of developmental stages including embryonic, chick and adult. In particular, cell lines may be derived from the embryonic cells, such as embryonic fibroblasts, germ cells, or individual organs, including neuronal, brain, retina, kidney, liver, heart, muscle, or extraembryonic tissues and membranes protecting the embryo. Chicken embryo fibroblasts (CEF) may be used. Examples of avian cell lines include avian embryonic stem cells (WO01/85938) and duck retina cells (WO05/042728). In particular, the EB66® cell line derived from duck embryonic stem cells is contemplated in the present invention (WO08/129058). Other suitable avian embryonic stem cells include the EBx® cell line derived from chicken embryonic stem cells, EB45, EB14 and EB14-074 (WO2006/108846). This EBx® cell line presents the advantage of being a stable cell line whose establishment has been produced naturally and did not require any genetic, chemical or viral modification. These avian cells are particularly suitable for growing influenza viruses.

According to a particular embodiment, the method of the invention uses EB66® cells.

Cell culture conditions (temperature, cell density, pH value, etc . . . ) are variable over a very wide range owing to the suitability of the cells employed and can be adapted to the requirements of particular virus growth conditions details. It is within the skilled in the art person's capabilities to determine the appropriate culture conditions, as cell culture is extensively documented in the art (see, for example, Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

In a specific embodiment, cells used in the method described in the present invention are cultured in serum-free and/or protein-free media. A "serum-free medium" (SFM) means a cell culture medium ready to use that does not require serum addition allowing cell survival and cell growth. This medium is not necessarily chemically defined and may contain hydrolyzates of various origin, from plant for instance. Such serum-free medium presents the advantage that contamination with adventitious viruses, mycoplasma or unknown infectious agents can be ruled out. "Protein-free" is understood to mean cultures in which multiplication of the cells occurs with exclusion of proteins, growth factors, other protein additives and non-serum proteins. Optionally trypsin or other proteases that may be necessary for viral growth may be added during virus infection. The cells growing in such culture naturally contain protein themselves.

Serum-free media are commercially available from numerous sources, for instance, VP SFM (Invitrogen Ref 11681-020), Opti-Pro (Invitrogen, Ref 12309-019), or EX-CELL (JHR Bioscience).

Prior to infection with the virus, cells are cultured around 37° C., more suitably at 36.5° C., at a pH ranging from 6.7 to 7.8, suitably around 6.8 to 7.5, and more suitably around 7.2. When cells are insect cells, the temperature prior to infection with the virus typically ranges from 25° C. to 29° C., suitably is 27° C.

According to the method of producing a virus of the present invention, the production of cell culture-based viruses generally includes the steps of a) providing a population of cells cultured in a culture medium; b) inoculating said cells with the virus of interest to be produced, so as to initiate the process of infection of the cells with the virus, and incubating or culturing the inoculated cells for a desired time period so as to allow virus replication and propagation, and c) collecting the produced virus. The high volumetric power input in accordance with the present invention is suitably applied during at least step b), and more suitably during steps a) and b). Accordingly, in one embodiment, in the method of producing a virus according to the present invention, a volumetric power input of at least 15 W/m³, at least 30 W/m³, at least 60 W/m³, at least 100 W/m³, or at least 120 W/m³ is applied to the cultured cells during steps a) and b).

The terms "inoculating/inoculation" and "inoculated cells" are to be understood in the sense of the present invention as the time of the addition of the virus of interest to the cells, and to the cells which have been added with the virus of interest, respectively. The terms "post-inoculation" are to be understood as the time duration after which the virus was added to the cells. In the rest of the specification, time "post-inoculation" is indicated in minutes, hours or days, such as for example, "2h post-inoculation", or "day 1 (D1) post-inoculation". The day during which the cells are inoculated with the virus shall be considered as day 0 (D0). The three successive steps of virus inoculation, virus replication, and virus propagation shall be understood as being part of the broader process of virus infection. High volumetric power input as defined in the present invention can be applied to the cell culture during any of the above steps. High volumetric power input in the sense of the present invention can be suitably applied to the cells while they are grown and cultured before being infected with the virus of interest. High volumetric power input in the sense of the present invention can be also suitably applied to the cells after they were inoculated with the virus and/or while they are left incubated so as to allow the virus to replicate and propagate. High volumetric power can be also suitably applied to the cells while they are grown and cultured before they are infected, after they were inoculated with the virus, and while they are left incubated so as to allow the virus to replicate and propagate. In one embodiment, high volumetric power input is applied to the cells used in the method according to the present invention after they were inoculated with the virus of interest and until the produced virus is collected. In a further embodiment, high volumetric power input is applied to the cells, while they are grown and cultured before being infected with the virus of interest, as well as after they were inoculated with said virus and until the produced virus is collected.

In order to produce large quantities of viruses, it may be advantageous to inoculate the cells with the virus of interest once cells have reached a high density. Usually, the inoculation is performed when the cell density is at least around $5\times10^6$ cells/ml, suitably $6\times10^6$ cells/ml, more suitably $7\times10^6$ cells/ml, more suitably $8\times10^6$ cells/ml, more suitably $9\times10^6$ cells/ml, or even higher, such as $10\times10^6$ cells/ml, $11\times10^6$ cells/ml, $12\times10^6$ cells/ml or $13\times10^6$ cells/ml, or even higher, such as $20\times10^6$ cells/ml, $25\times10^6$ cells/ml, or $30\times10^6$ cells/ml. In one embodiment of the method according to the invention, the cell density reached before virus infection takes place is at least $8\times10^6$ cells/ml, $9\times10^6$ cells/ml, $10\times10^6$ cells/ml, $11\times10^6$ cells/ml, $12\times10^6$ cells/ml or $13\times10^6$ cells/ml. In another embodiment, the cell density reached before virus infection takes place is at least $20\times10^6$ cells/ml, $25\times10^6$ cells/ml, or $30\times10^6$ cells/ml. Such levels of high density may be advantageously reached using a perfusion system for the cell culture. The optimal cell density for obtaining the highest virus production may vary according to the cell type used for the virus propagation. Standard techniques of protein detection, such as a Western-blot analysis, or SRD assay for influenza virus, or CPE as described above, may also be used for determining the optimal cell density range required to obtain an optimized virus yield.

In order to produce large quantities of viruses, it may also be advantageous to implement a virus adsorption phase. By "adsorption phase", it is meant that the cells are inoculated with the virus at high density, so as to favour the adsorption of the virus to the cell membranes, for a short period of time, before cell density is decreased for the rest of the infection period until the virus is collected. For example, the inoculation of the cells with the virus is performed when the cell density is at least $8\times10^6$ cells/ml, suitably at least $9\times10^6$ cells/ml, suitably at least $10\times10^6$ cells/ml, suitably at least $11\times10^6$ cells/ml, suitably at least $12\times10^6$ cells/ml, more suitably at least $13\times10^6$ cells/m, or even higher, such as $20\times10^6$ cells/ml, $25\times10^6$ cells/ml, or $30\times10^6$ cells/ml. Suitably 30 min, more suitably 45 min, more suitably 1 h, 1 h30, or 2 h post-inoculation with the virus, the inoculated cells are diluted by a factor ranging from 2 to 5, suitably 3, for the rest of the infection process, i.e. for further incubation before the produced virus is collected. Alternatively, at the end of the adsorption phase, the inoculated cells are diluted so as to obtain a final cell density ranging from 3 to $5\times10^6$ cells/ml, suitably $4\times10^6$ cells/ml, for the rest of the infection process, i.e. for further incubation before the produced virus is collected.

In an alternative embodiment, when the cell density is at least $8\times10^6$ cells/ml, at least $9\times10^6$ cells/ml, at least $10\times10^6$ cells/m, at least $11\times10^6$ cells/ml, at least $12\times10^6$ cells/ml, at least $13\times10^6$ cells/ml, at least $20\times10^6$ cells/ml, at least $25\times10^6$ cells/ml, or at least $30 \times 10^6$ cells/ml, the cells are inoculated with the virus, and immediately after inoculation, the inoculated cells are diluted, either by a factor ranging from 2 to 5, suitably 3, or so as to obtain a final cell density ranging from 3 to $5\times10^6$ cells/ml, suitably $4\times10^6$ cells/ml, for the rest of the infection process, i.e. for further incubation before the produced virus is collected.

When an adsorption phase is implemented, the volumetric power input may be suitably maintained at a low level, such as for instance, at a value ranging from 2 to 10 $W/m^3$, from 4 to 8 $W/m^3$, suitably at 7 $W/m^3$, during said phase, i.e. after the cells were inoculated with the virus of interest and before the inoculated cells were diluted. Accordingly, in one embodiment of the invention, the method of producing a virus in cell culture comprises at least the steps of a) providing a population of cells cultured in a culture medium, b) infecting the population of cells with the virus by i. inoculating the population with the virus when the cell density is at least $8\times10^6$ cells/ml, at least $9\times10^6$ cells/ml, at least $10\times10^6$ cells/ml, at least $11\times10^6$ cells/ml, at least $12\times10^6$ cells/ml, or at least $13\times10^6$ cells/ml for 30 min, 45 min, 1 h, 1 h30, or 2 h, and then diluting inoculated cells by a factor ranging from 2 to 5, or a factor 3, or alternatively, so that the final cell density obtained ranges from $3\times10^6$ cells/ml to $5\times10^6$ cells/ml, suitably $4\times10^6$ cells/ml and ii. incubating the diluted inoculated population so as to allow the virus to replicate and propagate, the volumetric power input applied to the cell culture being at least 15 $W/m^3$, at least 30 $W/m^3$, at least 60 $W/m^3$, at least 100 $W/m^3$, or at least 120 $W/m^3$, before the cells are inoculated with the virus, and then reduced to a value ranging from 2 to 10 $W/m^3$, 4 to 8 $W/m^3$, or 7 $W/m^3$, after the cells were inoculated and before the inoculated cells are diluted, and increased to at least 15 $W/m^3$, at least 30 $W/m^3$, at least 60 $W/m^3$, at least 100 $W/m^3$, or at least 120 $W/m^3$ after the inoculated cells were diluted and until the produced virus is collected. Alternatively, the volumetric power input can be maintained at a constant value through the adsorption phase. Accordingly, in a further embodiment, the volumetric power input applied to the cell culture according to the present invention is maintained at at least 15 $W/m^3$, at least 30 $W/m^3$, at least 60 $W/m^3$, at least 100 $W/m^3$, or at least 120 $W/m^3$, through the successive steps of providing a population of cells cultured in a cell culture medium, inoculating said population with the virus of interest for 30 min, 45 min, 1 h, 1 h30, or 2 h, diluting the inoculated cells according to the above conditions, and incubating the diluted inoculated population.

The inoculation can be carried out at an MOI (Multiplicity Of Infection) of about $10^{-1}$ to $10^{-7}$, suitably about $10^{-2}$ to $10^{-6}$, and more suitably, about $10^{-5}$.

The temperature and pH conditions for virus infection may vary. Temperature may range from 32° C. to 39° C. depending on the virus type. For influenza virus production, cell culture infection may vary depending on the strain which is produced. Influenza virus infection is suitably performed at a temperature ranging from 32° C. to 35° C., suitably at 33° C. In one embodiment, the virus infection occurs at 33° C. In an alternative embodiment, the virus infection takes place at 35° C. Proteases, typically trypsin, may be added to the cell culture depending on the virus strain, to allow viral replication. The protease can be added at any suitable stage during the culture. Tryspin is preferably of non-animal origin, that is to say the protease is not purified from an animal source. It is suitably recombinantly produced in a micro-organism, such as bacterial, yeast or plant. Suitable examples of recombinant trypsin are Trypzean, a recombinant trypsin produced in corn (Prodigen, 101 Gateway Blvd, Suite 100 College Station, Tex. 77845. Manufacturer code : TRY), or TrpLE (Invitrogen) which is a trypsin-like enzyme expressed in fungus (WO2004/020612). In one embodiment, trypsin is added at the same time as the virus is inoculated to the cells, i.e. trypsin is added at day 0 (D0). In a further embodiment, trypsin is further added at different time points post-inoculation, such as for instance, at day 1 (D1) and/or day 4 (D4) post-inoculation. In an alternate embodiment, trypsin is further added every day post-virus inoculation until the produced virus is collected.

Once infected, cells may release into the culture medium newly formed virus particles, due to spontaneous lysis of host cells, also called passive lysis. Therefore, in one embodiment, cell-produced viral harvest may be provided any time after virus inoculation by collecting the cell culture medium. This mode of harvesting is particularly suitable when it is desired to harvest cell-produced virus at different time points after virus inoculation, and pooling the different harvests, if needed.

Alternatively, after virus infection, cell culture-based virus may be harvested by employing external factor to lyse host cells, also called active lysis. However, contrary to the previous one, such a harvesting mode requires that the cell-derived viral harvest be collected at a single time point, as actively lysing the cells will immediately terminate the cell culture.

Methods that can be used for active cell lysis are known to the person skilled in the art. Useful methods in this respect are for example, freeze-thaw, solid shear, hypertonic and/or hypotonic lysis, liquid shear, high-pressure extrusion, detergent lysis, or any combination thereof.

According to one embodiment, cell culture-based viral harvest may be provided any time after virus inoculation by collecting the cell culture supernatants, lysing the inoculated cells or both.

Before harvesting, cell infection may last for 2 to 10 days. According to a specific embodiment, culture supernatants from days 3, 4 and 5 post-inoculation are harvested and pooled for further downstream processing (virus isolation or virus purification). According to a distinct embodiment, cell culture supernatant is collected from day 5 post-inoculation. The optimal time to harvest the cell-produced virus is usually based on the determination of the infection peak. For example, the CPE (CytoPathic Effect) is measured by monitoring the morphological changes occurring in host cells after virus inoculation, including cell rounding, disorientation, swelling or shrinking, death, detachment from the surface. The detection of a specific viral antigen may also be monitored by standard techniques of protein detection, such as a Western-blot analysis. Harvest can then be collected when the desired detection level is achieved. In the particular case of influenza virus, the content of HA may be monitored any time post-inoculation of the cells with the virus, by the SRD assay (Wood, J M, et al. (1977). J. Biol. Standard. 5, 237-247), which is a technique familiar to a person skilled in the art. Additionally, the SRD assay may also be used for determining the optimal cell density range required to obtain an optimized virus yield.

In the context of the present invention, the cell culture phase is to be understood as encompassing any step preceding the virus collecting step, while the virus purification phase is to be understood as encompassing any step following said collecting step.

According to the invention, after production in cell culture, the virus is purified. Any suitable step or technique known in the field of virus purification may be suitably implemented during the method of the invention after the produced virus is collected. In one embodiment, the method of the invention comprises at least one step selected from viral harvest clarification, ultrafiltration/diafiltration, ultracentrifugation and chromatography, or any combination thereof. Depending on the purity level that is desired, the above steps may be combined in any way.

In a specific embodiment, during the virus purification phase, the method of the invention comprises at least a viral harvest clarification step, an ultrafiltration/diafiltration step thereby providing a retentate and an ultracentrifugation step.

After collecting the virus-containing cell culture medium of infected cells, the provided viral harvest is typically clarified in order to separate the virus from the cellular material, such as intact cells or cell debris. Clarification may be done by a filtration step, typically a microfiltration step, i.e. using filters having a pore size typically between 0.1 μm and 10 μm. Suitable filters may utilize cellulose filters, regenerated cellulose filters, cellulose fibers combined with inorganic filter aids, cellulose filter combined with inorganic filter aids and organic resins, or any combination thereof, and polymeric filters. Although not required, a multiple filtration process may be carried out, like a two- or three-stage process consisting, for instance, in sequentially and progressively removing impurities according to their size, using filters with appropriate nominal pore size, in particular, filters with decreasing nominal pore size, allowing to start removing large precipitates and cell debris. In addition, single stage operations employing a relatively tight filter or centrifugation may also be used for clarification. More generally, any clarification approach including, but not limited to, direct flow filtration or "dead-end" filtration, depth filtration, tangential flow filtration or crossflow filtration, or centrifugation, which provide a filtrate of suitable clarity to not foul the membrane and/or resins in subsequent steps, will be acceptable to use in the clarification step of the present invention. In one embodiment, the viral clarification step is performed by depth filtration, in particular, using a three-stage train filtration composed, for example, of three different depth filters with nominal porosities of 5 μm-0.5 μm-0.2 μm. In another embodiment, the viral harvest is clarified by microfiltration, optionally preceded by a centrifugation step as pre-clarification. In particular embodiments wherein the method of producing a virus, such as influenza virus, according to the invention comprises a clarification step of microfiltration during the step d) of purification, the virus yield, such as HA yield for influenza virus, obtained after said clarification step is at least 65%, 66%, 67%, 68%, 69%, 70%, 71%, 72%, 73%, 74%, 75%, 76%, 77%, 78%, 79%, 80%, 85%, 90% or more.

According to the present invention, during the virus purification phase of the method of the present invention, the viral harvest may also be subject to ultrafiltration (sometimes referred to as diafiltration when used for buffer exchange), for concentrating the virus and/or buffer exchange. This step is particularly advantageous when the virus to be purified is diluted, as is the case, for example, when pooling viral harvest collected by perfusion over a few days post-inoculation. The process used to concentrate the virus and/or exchange buffer according to the method of the present invention can include any filtration process where the concentration of virus is increased by forcing diluent to be passed through a filter in such a manner that the diluent is removed from the virus suspension whereas the virus is unable to pass through the filter and thereby remains in concentrated form in the virus preparation.

If using membranes or filters which are not neutral but positively charged, it may be useful to implement an additional step of rinsing said membrane or filter with a rinsing buffer comprising salts to elute the virus fraction which may have been retained due to ionic interactions with the membrane or filter. One example of suitable salt which may be included in the rinsing buffer is sodium chloride (NaCl), which may be present at a concentration ranging from 0.1M to 2M, in particular, from 0.5M to 1.5M, suitably 1M. In one embodiment of the invention, when clarification is performed by membrane filtration, whether it is pre-clarification or clarification, said clarification comprises a membrane rinsing step with a buffer comprising NaCl, in particular, NaCl 1M.

Ultrafiltration may comprise diafiltration which is an ideal way for removal and exchange of salts, sugars, non-aqueous solvents, removal of material of low molecular weight, of rapid change of ionic and/or pH environments. Microsolutes are removed most efficiently by adding solvent to the solution being ultrafiltered at a rate equal to the ultrafiltration rate. This washes microspecies from the solution at a constant volume, isolating the retained virus. Diafiltration is particularly advantageous when a downstream step requires that a specific buffer be used in order to get an optimal reaction. For example, implementing a diafiltration step before degrading host cell nucleic acids with an endonuclease may allow performing the endonuclease reaction in a buffer specific and optimal for that endonuclease. Concentration and diafiltration may also be implemented at any suitable step of the purification process, when it is wanted to remove undesirable compounds, such as sucrose, after a sucrose gradient ultracentrifugation, or such as formaldehyde, after a step of virus inactivation with formaldehyde. The system is composed of three distinct process streams: the feed solution (comprising the virus), the permeate and the retentate. Depending on the application, filters with different pore sizes may be used. In the present invention, the retentate contains the virus and can be used for further purification steps, if desired. The membrane composition may be, but is not limited to, regenerated cellulose, polyethersulfone, polysulfone, or derivatives thereof. The membranes can be flat sheets (also called flat screens) or hollow fibers.

In one embodiment, the virus purification phase of the method of the invention comprises at least one ultrafiltration/diafiltration step, suitably at least two ultrafiltration/diafiltration steps.

Depending on what application is the cell culture-produced virus purified for, it may be desirable also to eliminate from the viral harvest host cell nucleic acids contaminants. In particular, when the purified virus is to be included in a vaccine, host cell nucleic acids should be degraded and eliminated from the purified virus. Nucleic acids degradation frequently occurs through the use of nucleases targeting RNA and DNA. A non-limiting example of a suitable nuclease for degrading host cell nucleic acids is Benzonase™. Benzonase™, or any other suitable nuclease, may be added at any suitable step of a virus purification process. In one embodiment, the method according to the invention comprises a nuclease degradation step, suitably a Benzonase™ treatment. For instance, a nuclease may be added to the retentate obtained after ultrafiltration of a clarified virus-containing cell-culture medium. Alternatively, host cell nucleic acids degradation may be achieved through a virus inactivation step with beta-propiolactone.

If desired, the virus obtained according to the present invention may be further purified using standard techniques employed for virus purification such as density gradient centrifugation, for instance sucrose gradient ultracentrifugation and/or chromatography, such as ion exchange chromatography. In one embodiment, the method according to the invention comprises at least one sucrose gradient centrifugation step. In a further embodiment, the purification phase of the method of the invention comprises at least a clarification step, such as for example, a centrifugation step followed by a microfiltration step, at least an ultrafiltration step, and a sucrose gradient centrifugation step. In particular embodiments wherein the method of producing a virus, such as influenza virus, according to the invention comprises at least one sucrose gradient centrifugation step during the step d) of purification, the load capacity on the rotor of the centrifuge is at least 40, at least 50, at least 60, or more, liters of viral harvest, or the "equivalent" amount, per litre of rotor, and the virus yield, such as HA yield for influenza virus, obtained after said sucrose gradient centrifugation step is at least 65%, 66%, 67%, 68%, 69%, 70%, 71%, 72%, 73%, 74%, 75%, 76%, 77%, 78%, 79%, 80%, 85%, 90% A or more.

According to the method of the invention, it may be possible to combine a purification step, such as sucrose gradient ultracentrifugation, with a virus splitting step. In particular, a splitting agent may be added to the sucrose gradient. This embodiment is particularly suitable, when it is desired to minimize the total number of steps of the method of the invention, as it allows, within a single operation, to both purify and split the virus. Hence, in certain embodiments, when at least one sucrose gradient ultracentrifugation is implemented, the sucrose gradient additionally comprises a splitting agent.

Alternatively, the virus splitting step of the method of the present invention, when implemented, is performed in batch.

At the end of the virus purification phase, the virus preparation obtained according to the method of the present invention may be suitably subject to sterile filtration, as is common in processes for pharmaceutical grade materials, such as immunogenic compositions or vaccines, and known to the person skilled in the art. Such sterile filtration can for instance suitably be performed by filtering the preparation through a 0.22 μm filter. After sterile preparation, the virus or viral antigens are ready for clinical use, if desired.

The immunogenic compositions, in particular vaccines, may generally be formulated in a sub-virion form, e.g. in the form of a split virus, where the lipid envelope has been dissolved or disrupted, or in the form of one or more purified viral proteins (subunit vaccine). As an alternative, the immunogenic compositions may include a whole virus, e.g. a live attenuated whole virus, or an inactivated whole virus.

Methods of splitting viruses, such as influenza viruses, are well known in the art (WO02/28422). Splitting of the virus is carried out by disrupting or fragmenting whole virus whether infectious (wild-type or attenuated) or non-infectious (inactivated) with a disrupting concentration of a splitting agent. Splitting agents generally include agents capable of breaking up and dissolving lipid membranes. Traditionally, split influenza virus was produced using a solvent/detergent treatment, such as tri-n-butyl phosphate, or diethylether in combination with Tween™ (known as "Tween-ether" splitting) and this process is still used in some production facilities. Other splitting agents now employed include detergents or proteolytic enzymes or bile salts, for example sodium deoxycholate. Detergents that can be used as splitting agents include cationic detergents e.g. cetyl thrimethyl ammonium bromide (CTAB), other ionic detergents, e.g. sodium lauryl sulphate (SLS), taurodeoxycholate, or non-ionic detergents such as Tween or Triton X-100, or combination of any two or more detergents.

In one embodiment, the splitting agent is deoxycholate. In another embodiment, the splitting agent is Triton X-100. In a further embodiment, the method according to the invention uses a combination of Triton X-100 and sodium lauryl sulfate as splitting agents.

The splitting process may be carried out as a batch, continuous or semi-continuous process. When implemented in batch, the split virus may require an additional step of purification, such as a chromatography step. It is not necessary to implement a splitting step as such, as it is possible to perform the splitting simultaneously to a purification step. For instance, a detergent may be added to the sucrose gradient aimed at purifying viral proteins by ultracentrifugation, as described above. In one embodiment, the method according to the invention comprises a splitting step performed in batch with a detergent, in particular, Triton X-100, in addition to at least one homogenization step.

For the safety of vaccines, it may be necessary to reduce infectivity of the virus suspension along different steps of the purification process. The infectivity of a virus is determined by its capacity to replicate on a cell line. Therefore, the method according to the present invention, optionally, includes at least one virus inactivation step. The inactivation may be performed by using, for instance, beta-propiolactone (BPL), formaldehyde, or UV, or any combination thereof, at any suitable step of the method. In one specific embodiment, the method according to the invention further comprises at least one BPL treatment step. In a specific embodiment, the method according to the invention further comprises at least one BPL treatment step and at least one formaldehyde treatment step. Formaldehyde and BPL may be used sequentially, in any order, for instance, formaldehyde is used after the BPL. In one embodiment, the formaldehyde treatment is followed by at least one homogenization step. When using, in particular, UV as the inactivation method, implementing homogenization of the virus preparation before UV irradiation, may help improve the efficiency of the virus inactivation. Viruses, or part of the viruses, which would be present within aggregates, whether virus aggregates or virus/cell aggregates may escape to irradiation because of burial within said aggregates, and, thus, non-accessibility of some virus or virus part to the inactivation agent. In one embodiment, the virus preparation obtained according to the method of the present invention is inactivated, for instance, by UV irradiation, and homogenization is performed immediately before said inactivation. The conditions of viral inactivation may vary and will be determined, in particular, by assessing the residual virus infectivity by measuring the Tissue Culture Infectious dose ($TCID_{50}$/ml).

Immunogenic compositions of the present invention, including vaccines, can optionally contain the additives customary for vaccines, in particular substances which increase the immune response elicited in a patient who receives the composition, i.e. so-called adjuvants.

In one embodiment, immunogenic compositions are contemplated, which comprise a virus or viral antigen of the present invention admixed with a suitable pharmaceutical carrier. In a specific embodiment, they comprise an adjuvant.

Adjuvant compositions may comprise an oil in water emulsion which comprise a metabolisable oil and an emulsifying agent. In order for any oil in water composition to be suitable for human administration, the oil phase of the emulsion system has to comprise a metabolisable oil. The meaning of the term metabolisable oil is well known in the art. Metabolisable can be defined as 'being capable of being transformed by metabolism' (Dorland's Illustrated Medical Dictionary, W. B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others.

A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil by virtue of the fact that it is an intermediate in the biosynthesis of cholesterol (Merck index, 10th Edition, entry no.8619). In a further embodiment of the invention, the metabolisable oil is present in the immunogenic composition in an amount of 0.5% to 10% (v/v) of the total volume of the composition.

The oil-in-water emulsion further comprises an emulsifying agent. The emulsifying agent may suitably be polyoxyethylene sorbitan monooleate. Further, said emulsifying agent is suitably present in the vaccine or immunogenic composition 0.125 to 4% (v/v) of the total volume of the composition.

The oil-in-water emulsion of the present invention optionally comprises a tocol. Tocols are well known in the art and are described in EP0382271. Suitably may be a tocol is alpha-tocopherol or a derivative thereof such as alpha-tocopherol succinate (also known as vitamin E succinate). Said tocol is suitably present in the adjuvant composition in an amount 0.25% to 10% (v/v) of the total volume of the immunogenic composition.

The method of producing oil-in-water emulsions is well known to the person skilled in the art. Commonly, the method comprises mixing the oil phase (optionally comprising a tocol) with a surfactant such as a PBS/TWEEN80™ solution, followed by homogenisation using a homogenizer, it would be clear to a man skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion. The adaptation could be achieved by routine experimentation comprising the measurement of the resultant emulsion until a preparation was achieved with oil droplets of the required diameter.

In an oil-in-water emulsion, the oil and emulsifier are in an aqueous carrier. The aqueous carrier may be, for example, phosphate buffered saline.

In particular, the oil-in-water emulsion systems of the present invention have a small oil droplet size in the sub-micron range. Suitably the droplet sizes will be in the range 120 to 750 nm, more particularly sizes from 120 to 600 nm in diameter. Even more particularly, the oil-in water emulsion contains oil droplets of which at least 70% by intensity are less than 500 nm in diameter, more particular at least 80% by intensity are less than 300 nm in diameter, more particular at least 90% by intensity are in the range of 120 to 200 nm in diameter.

The oil droplet size, i.e. diameter, according to the present invention is given by intensity. There are several ways of determining the diameter of the oil droplet size by intensity. Intensity is measured by use of a sizing instrument, suitably by dynamic light scattering such as the Malvern Zetasizer 4000 or suitably the Malvern Zetasizer 3000HS. A detailed procedure is given in Example II.2. A first possibility is to determine the z average diameter ZAD by dynamic light scattering (PCS-Photon correlation spectroscopy); this method additionally give the polydispersity index (PDI), and both the ZAD and PDI are calculated with the cumulants algorithm. These values do not require the knowledge of the particle refractive index. A second mean is to calculate the diameter of the oil droplet by determining the whole particle size distribution by another algorithm, either the Contin, or NNLS, or the automatic "Malvern" one (the default algorithm provided for by the sizing instrument). Most of the time, as the particle refractive index of a complex composition is unknown, only the intensity distribution is taken into consideration, and if necessary the intensity mean originating from this distribution.

The adjuvant compositions may further comprise a Toll like receptor (TLR) 4 agonist. By "TLR4 agonist" it is meant a component which is capable of causing a signalling response through a TLR4 signalling pathway, either as a direct ligand or indirectly through generation of endogenous or exogenous ligand (Sabroe et al, JI 2003 p1630-5). The TLR 4 may be a lipid A derivative, particularly monophosphoryl lipid A or more particularly 3 Deacylated monophoshoryl lipid A (3D-MPL).

3D-MPL is available under the trademark MPL® by GlaxoSmithKline Biologicals North America and primarily promotes CD4+ T cell responses with an IFN-g (Th1) phenotype. It can be produced according to the methods disclosed in GB 2 220 211 A. Chemically it is a mixture of 3-deacylated monophosphoryl lipid A with 3, 4, 5 or 6 acylated chains. In particular, in the adjuvant compositions of the present invention small particle 3 D-MPL is used. Small particle 3 D -MPL has a particle size such that it may be sterile-filtered through a 0.22 µm filter. Such preparations are described in International Patent Application No. WO 94/21292. Synthetic derivatives of lipid A are known and thought to be TLR 4 agonists including, but not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S, 9 R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-, 9R)-3-[(R) -dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127)

Other TLR4 ligands which may be used are alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants. In addition, further suitable TLR-4 agonists are disclosed in US2003/0153532 and US2205/0164988.

The invention is particularly suitable for preparing influenza virus immunogenic compositions, including vaccines. Various forms of influenza virus are currently available. They are generally based either on live virus or inactivated virus. Inactivated vaccines may be based on whole virions, spilt virions or purified surface antigens (including HA). Influenza antigens can also be presented in the form of virosomes (nucleic acid-free viral-like liposomal particles).

Virus inactivation methods and splitting methods have been described above and are applicable to influenza virus.

Influenza virus strains for use in vaccines change from season to season. In the current inter-pandemic period, vaccines typically include two influenza A strains and one influenza B strain. Trivalent vaccines are typical, but higher valence, such as quadrivalence, is also contemplated in the present invention. The invention may also use HA from pandemic strains (i.e. strains to which the vaccine recipient and the general human population are immunologically naïve), and influenza vaccines for pandemic strains may be monovalent or may be based on a normal trivalent vaccine supplemented by a pandemic strain.

Compositions of the invention may include antigen(s) from one or more influenza virus strains, including influenza A virus and/or influenza B virus. In particular, a trivalent vaccine including antigens from two influenza A virus strains and one influenza B virus strain is contemplated by the present invention. Alternatively a quadrivalent vaccine including antigens from two influenza A virus strains and two influenza B virus strains is also within the scope of the present invention.

The compositions of the invention are not restricted to monovalent compositions, i.e. including only one strain type, i.e. only seasonal strains or only pandemic strains. The invention also encompasses multivalent compositions comprising a combination of seasonal strains and/or of pandemic strains. In particular, a quadrivalent composition, which may be adjuvanted, comprising three seasonal strains and one pandemic strain falls within the scope of the invention. Other compositions falling within the scope of the invention are a trivalent composition comprising two A strains and one B strain, such as H1N1, H3N2 and B strains, and a quadrivalent composition comprising two A strains and two B strains of a different lineage, such as H1N1, H3N2, B/Victoria and B/Yamagata.

HA is the main immunogen in current inactivated influenza vaccines, and vaccine doses are standardized by reference to HA levels, typically measured by SRD. Existing vaccines typically contain about 15 µg of HA per strain, although lower doses can be used, e.g. for children, or in pandemic situations, or when using an adjuvant. Fractional doses such as a half (i.e. 7.5 µg HA per strain) or a quarter have been used, as have higher doses, in particular, 3× or 9× doses. Thus immunogenic compositions of the present invention may include between 0.1 and 150 µg of HA per influenza strain, particularly, between 0.1 and 50 µg, e.g. 0.1-20 µg, 0.1-15 µg, 0.1-10 µg, 0.1-7.5 µg, 0.5-5 µg, etc. Particular doses include about 15, about 10, about 7.5, about 5 µg per strain, about 3.8 µg per strain and about 1.9 µg per strain.

Once an influenza virus has been purified for a particular strain, it may be combined with viruses from other strains to make a trivalent vaccine, for example, as described above. It is more suitable to treat each strain separately and to mix monovalent bulks to give a final multivalent mixture, rather than to mix viruses and degrade DNA and purify it from a multivalent mixture.

The invention will be further described by reference to the following, non-limiting, examples.

EXAMPLE I

Influenza Virus Production Using A High Volumetric Power

EB66® cells were seeded in a 200 L disposable bioreactor (Cultibag STR from Sartorius AG which includes a pitched-blade impeller, or a Rushton turbine, where appropriate) at a density of about $0.4 \times 10^6$ cells/ml in a total volume of 65 L, and grown in suspension in batch mode at 36.5° C. at an agitation speed of 105 rpm corresponding to the application of a volumetric power input of at least 30 W/m$^3$ (No. 039, No. 048, No. 052, No. 058, No. 044, No. 046, and No. 043), or 135 rpm corresponding to the application of a volumetric power input of at least 120 W/m$^3$ (No. 053 and No. 057), or 65 rpm corresponding to the application of a volumetric power input of at least 7 W/m$^3$ (No. 025, No. 026, No. 027 and No. 031). The volumetric power input of at least 30 W/m$^3$ was achieved using the disposable bioreactor including a pitched-blade impeller, while the power input of at least 120 W/m$^3$ was achieved using the disposable bioreactor including a Rushton turbine.

After 3 days of growth, the cell density reached at least $9 \times 10^6$ cells/ml. At this point in time, cells were inoculated with a solution comprising H5N1 Influenza virus at a Multiplicity of Infection (MOI) of $1\times10^{-5}$ and trypsin (30 mrPu/ml TrpLE from Invitrogen), which is considered Day 0 (D0), and the temperature was switched at 35° C. 1 h30 post-inoculation, the inoculated cell suspension was subject to a dilution by a factor 3 by adding fresh medium up to a total volume of 200 L. During the above 1 h30 time period, the volumetric power input was either reduced to 7 W/$m^3$ (No. 039, No. 048, No. 052, No. 058, No. 044, No. 046, No. 043, No. 053 and No. 057) or maintained at 7 W/$m^3$ (No. 025, No. 026, No. 027 and No. 031).

Immediately after the inoculated cells were diluted, the volumetric power input was increased again to at least 30 W/$m^3$ (No. 039, No. 048, No. 052, No. 058, No. 044, No. 046, and No. 043), or at least 120 W/$m^3$ (No. 053 and No. 057) and maintained at such levels, or maintained at 7 W/$m^3$ (No. 025, No. 026, No. 027 and No. 031), until the virus-containing culture medium was collected, 5 days post-virus inoculation, producing thus the viral harvest. Trypsin (10 mrPu/ml TrpLE from Invitrogen) was further added at Day 1 (D1) and Day 4 (D4) post-virus inoculation.

The viral harvest was then purified as described below.

EXAMPLE II

Effect of a High Volumetric Power on Microfiltration

Once harvested, the viral harvest was pre-clarified by continuous centrifugation at 10500 rpm at 90 L/h, producing thus the pre-clarified viral harvest.

The pre-clarified harvest was then subject to a microfiltration step using a 0.45 μm flat-sheet membrane (Sartorius AG), at constant TMP (Trans Membrane Pressure) and feed flow rate (3 psi and 600 L/m²/h, respectively), producing thus the clarified viral harvest.

The influenza virus yield was evaluated at the microfiltration step by measuring the HA content before and after said step according to the SRD assay, as described below in Example IV. Results are presented in Table 1 in the form of percentages to be compared to the control value 100% representing the total HA amount present in the starting material, i.e. present in the pre-clarified viral harvest before microfiltration.

TABLE 1

HA yield after microfiltration - Low volumetric power versus high volumetric power

| Experiment No. | Volumetric Power Input V/m³ | Cell Density at virus inoculation ×10⁶ cells/ml | Viral Production at D5 pi * μg HA/ml | Microfiltration HA Yield % |
|---|---|---|---|---|
| 039 | 30 | 12 | 67 | 71 |
| 052 | 30 | 12.6 | 92 | 82 |
| 058 | 30 | 11 | 82 | 81 |
| Average | | | 80 | 78 |
| ** Std Dev | | | | 6 |
| 053 | 120 | 12.6 | 88 | 70 |
| 057 | 120 | 11 | 79 | 63 |
| Average | | | 84 | 67 |
| ** Std Dev | | | | 5 |
| 025 | 7 | 13 | 75 | 41 |
| 026 | 7 | 11 | 57 | 91 |
| 027 | 7 | 9.3 | 82 | 77 |
| 031 | 7 | 13 | 81 | 44 |
| Average | | | 74 | 63 |
| ** Std Dev | | | | 25 |

* pi: post-virus inoculation
** Std Dev: Standard Deviation

Results—Conclusions

While increasing the volumetric power input during the cell culture phase (30 W/m³ versus 7 W/m³) had no impact on the HA yield present in the collected viral harvest (see Table 1, fourth column "Viral Production at D5 pi"), a positive impact was observed on the HA yield achieved at the subsequent microfiltration step. Not only is the HA yield obtained after microfiltration higher when the volumetric power input is higher (see the respective average rows), but the values obtained from one experiment to another are also more consistent and less variable (see the respective Std Dev rows—6 versus 25 when volumetric power input is 30 or 7, respectively). These results indicate that a higher volumetric power during the upstream cell culture phase results in improved and more consistent HA yields during the downstream virus purification phase.

EXAMPLE III

Effect of High Volumetric Power on Sucrose Gradient Ultracentrifugation

Cells were grown and infected with H5N1 Influenza virus, and the virus was harvested as described in the above Example I.

The viral harvest was pre-clarified, and the pre-clarified harvest was subject to microfiltration as described in the Example II.

The clarified viral harvest was then concentrated 10-fold by ultrafiltration with a 750 kD hollow fiber membrane made of polysulphone (GE Healthcare) and diafiltrated against 5 volumes of PBS containing 125 mM citrate pH 7.4 at constant TMP (Trans Membrane Pressure) and feed flow rate (3 psi and 35 $L/m^2/h$, respectively).

The ultrafiltration retentate was then subject to a sucrose gradient ultracentrifugation step, wherein virus and contaminants migrate into the gradient until reaching their respective density. Influenza virus has a density of approximately 1.19 $g/cm^3$ and will thus sediment in the gradient where the sucrose concentration equals the density of the virus (approximately 43% sucrose). After formation of a continuous linear gradient from 0 to 55% sucrose in the rotor of the centrifuge, the ultrafiltration retentate was loaded into said rotor at a loading capacity of the retentate-equivalent corresponding to 30 L harvest per L of rotor (No. 039, No. 043, No. 032, No. 033, No. 028 and No. 029), or 50-60 L harvest per L of rotor (No. 044A, No. 044B, No. 046, No. 048, No. 025, No. 026, No. 027, No. 031), as indicated in Tables 2 and 3. When the entire sample is loaded, a banding time of 1 h allowed the virus to reach its density and concentrate within the sucrose gradient before the centrifuge was stopped and the sucrose gradient was unloaded and fractionated. The viral particles were concentrated within a few fractions. The product fractions were in PBS pH 7.4 containing 125 mM citrate and sucrose. The purified whole virion was pooled from the percentage of sucrose ranging from approximately 30 to 50%. This range has been determined on the basis of profiles from SDS-PAGE and from Western Blot analysis using anti-HA antibodies.

The influenza virus yield was evaluated at the sucrose gradient ultracentrifugation step by measuring the HA content before and after said step according to the SRD assay, as described below in Example IV. Results are presented in Table 2 and Table 3 in the form of percentages to be compared to the control value 100% representing the total HA amount present in the starting material, i.e. present in the ultrafiltration retentate before the sucrose gradient ultracentrifugation.

TABLE 2

HA yield after sucrose gradient ultracentrifugation at a load capacity of 30 L harvest per L of rotor

| Experiment No. | Volumetric Power Input $V/m^3$ | Rotor Volume L | Load capacity L Harvest/ L rotor | HA Yield % |
|---|---|---|---|---|
| 039 | 30 | 3.2 | 30 | 54 |
| 043A | 30 | 3.2 | 30 | 70 |
| 043B | 30 | 1.6 | 30 | 69 |
| Average | | | | 72 |

TABLE 2-continued HA yield after sucrose gradient ultracentrifugation
at a load capacity of 30 L harvest per L of rotor

| Experiment No. | Volumetric Power Input V/m³ | Rotor Volume L | Load capacity L Harvest/ L rotor | HA Yield % |
|---|---|---|---|---|
| * Std Dev | | | | 17 |
| 032 | 7 | 3.2 | 30 | 95 |
| 033 | 7 | 3.2 | 30 | 78 |
| 028 | 7 | 3.2 | 30 | 87 |
| 029 | 7 | 3.2 | 30 | 67 |
| Average | | | | 82 |
| * Std Dev | | | | 12 |

* Std Dev: Standard Deviation

The indicated Load Capacity (30) corresponds to the ultrafiltration retentate-equivalent of viral harvest litres collected during step c) of the method of the invention loaded per litre of rotor of the centrifuge.

Results—Conclusions

At a loading capacity of 30 L Harvest per L of rotor, the average HA yield achieved after sucrose gradient ultracentrifugation is within the same acceptable range, i.e. 72-82%, whether the volumetric power input is 7 $V/m^3$ or 30 $V/m^3$.

TABLE 3

HA yield after sucrose gradient ultracentrifugation at a load capacity of 50-60 L harvest per L of rotor

| Experiment No. | Volumetric Power $V/m^3$ | Rotor Volume L | Load Capacity L Harvest/ L rotor | HA Yield % |
|---|---|---|---|---|
| 044A | 30 | 1.6 | 60 | 75 |
| 044B | 30 | 1.6 | 60 | 72 |
| 046 | 30 | 3.2 | 50 | 63 |
| 048 | 30 | 1.6 | 50 | 74 |
| Average | | | | 71 |
| * Std Dev | | | | 5 |
| 025 | 7 | 3.2 | 60 | 12 |
| 026 | 7 | 3.2 | 60 | 29 |
| 027 | 7 | 1.6 | 60 | 35 |
| 031 | 7 | 1.6 | 60 | 50 |
| Average | | | | 31 |
| * Std Dev | | | | 15 |

* Std Dev: Standard Deviation

The indicated Load Capacity (50 or 60) corresponds to the ultrafiltration retentate-equivalent of viral harvest litres collected during step c) of the method of the invention loaded per litre of rotor of the centrifuge.

Results—Conclusions

At a higher loading capacity of 50-60 L Harvest per L of rotor, when the volumetric power input is 7 $V/m^3$, i.e. at a low volumetric power input, the average HA yield achieved after sucrose gradient ultracentrifugation significantly dropped (see Table 3, 31%), as opposed to the HA yield achieved at a loading capacity of 30 L Harvest per L of rotor with a similar low volumetric power input (see Table 2, 82%). On the contrary, when the volumetric power input was increased to 30 $V/m^3$, the average HA yield achieved after sucrose gradient ultracentrifugation at the higher loading capacity of 50-60 L Harvest per L of rotor was maintained at the same acceptable range (see Table 3, 71%). This indicates that increasing the volumetric power input during the cell culture phase (30 $W/m^3$ versus 7 $W/m^3$) allows to load twice more harvest volume, or harvest volume equivalent, on the rotor used for the sucrose gradient ultracentrifugation step while keeping the same acceptable range of HA yield. The loading capacity on a centrifuge directly impacts the number of centrifuges required to operate at large scale. The higher the load capacity is, the lower the number of centrifuges needed is.

EXAMPLE IV

SRD Method Used To Measure Ha Content

Glass plates (12.4-10 cm) were coated with an agarose gel containing a concentration of anti-influenza HA serum that is recommended by NIBSC. After the gel has set, 72 sample wells (3 mm diameter) were punched into the agarose. 10 µl of appropriate dilutions of the reference and the sample were loaded in the wells. The plates were incubated for 24 hours at room temperature (20 to 25° C.) in a moist chamber. After that, the plates were soaked overnight with NaCl solution and washed briefly in distilled water. The gel was then pressed and dried. When completely dry, the plates were stained on Coomassie Brillant Blue solution for 10 minutes and destained twice in a mixture of methanol and acetic acid until clearly defined stained zones become visible. After drying the plates, the diameter of the stained zones surrounding antigen wells was measured in two directions at right angles. Alternatively equipment to measure the surface can be used. Dose-response curves of antigen dilutions against the surface were constructed and the results were calculated according to standard slope-ratio assay methods (Finney, D. J. (1952). Statistical Methods in Biological Assay. London: Griffin, Quoted in: Wood, J M, et al (1977). J. Biol. Standard. 5, 237-247)

We claim:

1. A method of producing a virus in cell culture comprising at least the steps of:

a) providing a population of cells in a cell culture medium, b) infecting the population of cells by:

i. inoculating the population of cells with the virus, and ii. incubating the inoculated population of cells so as to allow the virus to replicate and propagate, c) collecting the produced virus, thereby providing a viral harvest, and d) purifying the virus, wherein a volumetric power input of at least 15 $W/m^3$, at least 30 $W/m^3$, at least 60 $W/m^3$, at least 100 $W/m^3$, or at least 120 $W/m^3$ is applied to the cell culture at least during step b) and wherein during step b) i, the volumetric power input is reduced to 2 to 10 $W/m^3$.

2. The method according to claim 1, wherein the volumetric power input is applied to the cell culture during step a) and step b).

3. The method according to claim 1, wherein the cell density of the cells reaches at least $8\times10^6$ cells/ml, at least $9\times10^6$ cells/ml, at least $10\times10^6$ cells/ml, at least $11\times10^6$ cells/ml, at least $12\times10^6$ cells/ml, or at least $13\times10^6$ cells/ml before the population of cells is inoculated with the virus.

4. The method according to claim 3, wherein during step b) the inoculated cells of step i. are diluted by a factor ranging from 2 to 5 immediately after the virus was inoculated, and left for further incubation.

5. The method according to claim 3, wherein during step b) the inoculated cells of step i. are diluted so as to obtain a cell density ranging from $3 \times 10^6$ cells/ml to $5 \times 10^6$ cells/m immediately after the virus was inoculated, and left for further incubation.

6. The method according to claim 3, wherein during step b) the virus is left incubated for 30 min, 45 min, 1 h, 1 h30, or 2 h after inoculation, before the inoculated cells are diluted by a factor ranging from 2 to 5, and left for further incubation.

7. The method according to claim 3, wherein during step b) the virus is left incubated for 30 min, 45 min, 1 h, 1 h30, or 2 h after inoculation, before the inoculated cells are diluted so as to obtain a cell density ranging from $3 \times 10^6$ cells/ml to $5 \times 10^6$ cells/ml, and left for further incubation.

8. The method according to claim 1, wherein trypsin is added to the cells during step b).

9. The method according to claim 8, wherein trypsin is added at the same time as the inoculation with the virus.

10. The method according to claim 9, wherein trypsin is further added at a day selected from the group consisting of:
  (A) D1 post-inoculation;
  (B) D4 post-inoculation; and
  (C) D1 and day D4 post-inoculation.

11. The method according to claim 9, wherein trypsin is further added every day post-virus inoculation until the produced virus of step c) is collected.

12. The method according to claims 1, wherein the produced virus of step c) is collected between 2 to 10 days post-virus inoculation.

13. The method according to claims 1, wherein the virus purifying step d) comprises at least one step selected from the group consisting of:
  (A) viral harvest clarification,
  (B) ultrafiltration/diafiltration,
  (C) ultracentrifugation and chromatography, or
  (D) any combination of (A)-(C).

14. The method according to claim 13, wherein the virus purifying step d) comprises at least a step of viral harvest clarification.

15. The method according to claim 14, wherein the viral harvest is clarified by microfiltration.

16. The method according to claim 13, wherein the virus purifying step d) comprises at least one step of sucrose gradient ultracentrifugation.

17. The method according to claim 1, wherein the virus purifying step d) comprises a step of virus inactivation.

18. The method according to claim 17, wherein the virus inactivation step is performed with beta-propiolactone.

19. The method according to claim 1, wherein the virus purifying step d) comprises a splitting step.

20. The method according to claim 1, further comprising a step of formulating the purified virus into a vaccine.

21. The method according to claim 1, wherein the virus is influenza virus.

22. The method according to claim 21, wherein the influenza virus is selected from the group consisting of: a H2 subtype, a H5 subtype, a H6 subtype, a H7 subtype, and a H9 subtype.

23. The method according to claim 21, wherein the influenza virus is selected from the group consisting of: a H1 subtype, a H3 subtype; or a B subtype.

24. The method according to claim 1, wherein the cells are selected from the group consisting of: mammalian and avian cells.

25. The method according to claim 1, wherein the cells are grown in suspension.

26. The method according to claim 1, wherein the cells are EB66® cells.

27. A method for the preparation of a vaccine comprising at least the step of admixing the virus obtained according to the method of claim 1 with a pharmaceutically acceptable carrier.

28. A method for preparing a vaccine comprising at least the following steps:
  a) providing a population of cells in a cell culture medium,
  b) infecting the population of cells by:
    i. inoculating the population with the virus, and
    ii. incubating the inoculated population so as to allow the virus to replicate and propagate,
  c) collecting the produced virus, thereby providing a viral harvest, and
  d) purifying the virus,
  wherein a volumetric power input of at least 15 W/m³, at least 30 W/m³, at least 60 W/m³, at least 100 W/m³, or at least 120 W/m³ is applied to the cell culture at least during step b),
  wherein during step b) i, the volumetric power input is reduced to 2 to 10 W/m³, and
  wherein subsequent to step b) i, the volumetric power input is increased to at least 15 W/m³, at least 30 W/m³, at least 60 W/m³, at least 100 W/m³, or at least 120 W/m³ after the inoculated cells are diluted and until the produced virus is collected,
  and formulating the purified virus into a vaccine.

* * * * *